United States Patent
Roturier et al.

(10) Patent No.: US 6,428,992 B1
(45) Date of Patent: Aug. 6, 2002

(54) PROCESS FOR THE PURIFICATION OF 1,3-PROPANEDIOL FROM A FERMENTATION MEDIUM

(75) Inventors: Jean-Michel Roturier, Chappelle d'Armentieres; Catherine Fouache, Sailly la Bourse, both of (FR); Elie Berghmans, Erps Kwerps (BE)

(73) Assignee: Roquette Freres, Lestrem (FR)

(*) Notice: Subject to any disclaimer, the term of this patent is extended or adjusted under 35 U.S.C. 154(b) by 0 days.

(21) Appl. No.: 09/712,787

(22) Filed: Nov. 14, 2000

(51) Int. Cl.[7] .................................................. C12P 7/18
(52) U.S. Cl. ...................... 435/158; 435/106; 435/115; 435/116; 562/513
(58) Field of Search ................................ 435/158, 106, 435/115, 116; 562/513

(56) References Cited

U.S. PATENT DOCUMENTS

| | | | |
|---|---|---|---|
| 5,008,473 A | | 4/1991 | Breitkopf et al. |
| 5,164,309 A | | 11/1992 | Gottschalk et al. |
| 5,202,476 A | * | 4/1993 | Tsuda et al. ................. 562/513 |
| 5,254,467 A | | 10/1993 | Kretschmann et al. |
| 5,686,276 A | * | 11/1997 | Laffend et al. ............. 435/158 |

FOREIGN PATENT DOCUMENTS

| WO | WO 96/35795 | 11/1996 |
|---|---|---|
| WO | WO 96/35796 | 11/1996 |
| WO | WO 98/21341 | 5/1998 |

OTHER PUBLICATIONS

D. C. Cameron et al., "Metabolic Engineering of Propanediol Pathways", Biotechnol. Prog., 1998, vol. 14, pp. 116–125, XP002067772.

K. W. Talmadge et al., "HPLC Separations of a Broad Spectrum of Small Molecular Weight Analytes on Cation–exchange Columns", American Laboratory, Dec. 1997, vol. 29, n° 24, pp. 37–43, XP000922955.

J. Malinowski, "Evaluation of Liquid Extraction Potentials for Downstream Separation of 1,3–propanediol", Biotechnol. Tech., 1999, vol. 13, pp. 127–130.

R. R. Broekhuis, et al "Recovery of Propylene Glyol from Dilute Aqueous Solutions via Reversible Reaction with Aldehydes", Ind. Eng. Chem. Res., 1994, vol. 33, pp. 3230–3237.

R. R. Broekhuis, "Recovery of Propylene Glycol from Dilute Aqueous Solutions by Complexation with Organoboronates in Ion–Pair Extractants", Ind. Eng. Chem. Res., 1996, vol. 35, pp. 1206–1214.

Günzel B. et al, "Microbial Production of Diols and their Recovery", Dechema Biotechnology Conferences 4, 1990, pp. 713–716.

P. Wittlich et al., "Bioconversion of Glycerol to 1,3–propanediol by Immobilized Bacteria", ECB9 Congress, Brussels, Jul. 1999, Session in Bioencapsulation Processes.

* cited by examiner

*Primary Examiner*—Christopher R. Tate
*Assistant Examiner*—Kailash C. Srivastava
(74) *Attorney, Agent, or Firm*—Henderson & Sturm LLP

(57) ABSTRACT

The present invention relates to a process for the purification of 1,3-propanediol from a fermentation medium of a 1,3-propanediol-producing microorganism, comprising 1,3-propanediol and fermentation coproducts consisting at least of glycerol, wherein the 1,3-propanediol-producing microorganism is separated from the other components of the fermentation medium to give a clarified aqueous solution, clarified aqueous solution is passed over a cation exchange resin to give at least one fraction comprising purified 1,3-propanediol and at least one fraction comprising the fermentation coproducts, and the 1,3-propanediol is recovered.

9 Claims, No Drawings

PROCESS FOR THE PURIFICATION OF 1,3-PROPANEDIOL FROM A FERMENTATION MEDIUM

FIELD AND OBJECTS OF THE INVENTION

The present invention relates to a process for the purification of 1,3-propanediol from a fermentation medium comprising 1,3-propanediol and fermentation coproducts.

The present invention relates more particularly to a process for the purification of 1,3-propanediol by subjecting a clarified aqueous solution originating from said fermentation medium to chromatography on a cationic resin to give at least one fraction comprising purified 1,3-propanediol and at least one fraction comprising the fermentation coproducts.

In the invention, "clarified aqueous solution" is understood as meaning the aqueous solution obtained after removal of the 1,3-propanediol-producing microorganisms from the fermentation medium.

Also, "fermentation coproducts" are understood as meaning the products resulting from a secondary metabolism, such as glycerol in particular, or the unconverted substrate, for example glucose or glycerol, or various residues originating from the nutrients in the fermentation medium or from the bacterial metabolism, such as acetic acid, ethanol or 2,3-butanediol.

The present invention relates even more particularly to a process for the purification of 1,3-propanediol by chromatography using a cationic resin whose cation is advantageously selected from the group consisting of lanthanum, lead, zinc, iron and aluminum.

Finally, the present invention relates to a treatment by microorganisms which specifically convert the glycerol to 1,3-propanediol, of said clarified aqueous solution and/or the fractions respectively containing glycerol and/or a mixture of glycerol and 1,3-propanediol, obtained by the chromatographic separation.

BACKGROUND OF THE INVENTION

The methods of purifying 1,3-propanediol from a fermentation medium which are known in the state of the art are principally based on a series of steps consisting in extracting the 1,3-propanediol from said fermentation medium with organic solvents and/or distilling it.

The conventional distillation techniques normally used in these purification processes require a large input of energy, which reflects on the cost of the final product purified in this way. This distillation point of 1,3-propanediol is in fact 214° C.

MALINOWSKI (for example in his article in *Biotechnology Techniques*, 1999, 13, pp 127–130) proposed a liquid-liquid extraction process with organic solvents to extract the 1,3-propanediol from dilute aqueous solutions containing it.

However, this purification process requires the handling of large quantities of solvents of the pentanol type (up to nonanol) or hexanal type (up to decanal) and, in particular, its 1,3-propanediol extraction and separation efficiency is too low.

MALINOWSKI moreover recognizes the need to turn to an alternative, more efficient method as 1,3-propanediol is too hydrophilic.

Another alternative, proposed by BROEKHUIS et al. in *Ind. Eng. Chim. Res.*, 1994, 33, pp. 3230–3237, was to use chemicals of the formaldehyde or acetaldehyde type to form a dioxolane derivative of the 1,3-propanediol, which then facilitates its solvent extraction.

However, although the process consumes less energy, the cost of the chemicals used makes the extraction and purification process prohibitive because of the additional need to regenerate the 1,3-propanediol from its dioxolane derivative.

Likewise, the processes for complexation of the 1,3-propandiol with organoborates, proposed by BROEKHUIS et al. in *Ind. Eng. Chim. Res.*, 1996, 35, pp. 1206–1214, demand substantial means to regenerate the 1,3-propandiol, making these extraction processes economically non-viable.

It is therefore apparent from all the above that there is an unsatisfied need for a process which is simple to carry out and makes it possible to purify 1,3-propanediol from the fermentation medium of a 1,3-propandiol-producing microorganism.

Anxious to develop a process which satisfies the practical constraints better than the process already in existence, the inventors have found that it is possible efficiently to purify 1,3-propanediol from said fermentation medium by a means which consists in performing a specific chromatographic separation of the components of the fermentation medium.

A process for the separation of 1,3-propanediol from a fermentation medium by chromatography has in fact been proposed by BÜNZEL et al. (for example in *DECHEMA BIOTECHNOLOGY Conferences*, 1990, 4 pt. B, pp. 713–716) and consists in employing adsorption techniques, especially adsorption on hydrophobic zeolites such as silicalite-1 or non-aluminous NaY zeolites, or even active charcoal.

However, the capacity of 1,3-propanediol to adsorb onto these supports is very mediocre; furthermore, some of the fermentation coproducts regrettably bind to said supports.

MORE DETAILED DESCRIPTION

The process according to the invention for the purification of 1,3-propanediol from a fermentation medium of a 1,3-propanediol-producing microorganism, comprising 1,3-propanediol and fermentation coproducts consisting at least of glycerol, is thus characterized in that:

a) the 1,3-propanediol-producing microorganism is separated from the other components of the fermentation medium to give a clarified aqueous solution;

b) said clarified aqueous solution is passed over a cation exchange resin to give at least one fraction comprising purified 1,3-propanediol and at least one fraction comprising the fermentation coproducts; and c) the 1,3-propanediol is recovered.

The 1,3-propanediol-producing microorganism is selected from the group of recombinant microorganisms which are capable e.g. of producing 1,3-propanediol from glucose, i.e. recombinant microorganisms of the *E. coli* or *S. cerevisiae* type, such as those described in patent applications WO 96/35796 and WO 98/21341.

The inventors have noticed that these microorganisms predominantly produce on the one hand 1,3-propanediol and on the other hand glycerol in particular as the fermentation coproduct. The fermentation medium may also contain some glucose which as not been completely consumed and a small amount of acetic acid.

The first step of the process according to the invention consists in separating the 1,3-propanediol-producing microorganisms from the other components of the fermentation medium to give a clarified aqueous solution.

This separation is effected by any technique otherwise known to those skilled in the art and can consist of a microfiltration or centrifugation of said microorganisms or a precipitation thereof with flocculants. These techniques can also be combined.

The preferred technique in the process according to the invention is that of microfiltration using a microfiltration membrane whose porosity is adapted to the size of the microorganisms in question, for example TECHSEP membranes of porosity 0.1 μm for 1,3-propanediol-producing recombinant microorganisms of the genus E. coli.

It is advantageously chosen to pass the resulting clarified aqueous solution through a column of charcoal and demineralize it on a strong cationic resin and then on a weakly and/or strongly basic anionic resin, for example of the acrylic type, employing the techniques widely known to those skilled in the art.

These steps make it possible to remove the cellular debris and the proteins resulting from any lysis of the 1,3-propanediol-producing microorganisms, and the effect of desalination is to remove the mineral load from the fermentation medium.

It can then be chosen to treat said clarified aqueous solution with a microorganism which converts the residual glycerol to 1,3-propanediol.

In such a case this microorganism is selected from the group consisting of microorganisms of the genera Klebsiella, Citrobacter, Clostridium, Lactobacillus, Ilyobacter, Pelobacter or Enterobacter, and is preferably a Citrobacter or a Clostridium.

In one particularly preferred embodiment of the process according to the invention, it is chosen to use this microorganism capable of converting the glycerol to 1,3-propanediol, in the free or immobilized form and preferably in the immobilized form.

It is possible to effect this immobilization with the aid of calcium alginate, for example as described in U.S. Pat. No. 5,164,309 for microorganisms of the genus Citrobacter, or to use the technology developed by GENIALAB BIO TECHNOLOGIE for microorganisms of the genus Clostridium (communication to the ECB9 congress, Brussels, July 1999, in the session of *Bioencapsulation processes*).

This step of conversion of the residual glycerol to 1,3-propanediol therefore makes it possible to increase the titre of 1,3-propanediol in the clarified solution and thus to reduce the glycerol component of the constituents of said clarified aqueous solution, thereby facilitating the actual chromatographic separation.

The second step of the process according to the invention consists in passing the clarified aqueous solution over a cation exchange resin.

The cation is advantageously selected from the group consisting of lanthanum, lead, iron, zinc and aluminum.

This step is carried out so as to give at least one fraction comprising purified 1,3-propanediol and at least one fraction comprising the fermentation coproducts.

It is arbitrary which way this chromatographic separation is performed. It can be carried out batchwise or by a continuous process.

This step can advantageously be carried out on a strongly acidic cation exchange resin of the polystyrenesulfonic acid type crosslinked with at least 4%, preferably at least 7%, of divinylbenzene.

Elution will be effected with water; this constitutes an important characteristic of the 1,3-propanediol purification process according to the invention since no organic solvent has to be used here. The process is therefore clean and satisfies the environmental protection standards.

In a first embodiment of the process according to the invention, it is preferable to load the resin with a cation selected from the group consisting of lanthanum, lead and iron.

The inventors have found that this choice of cations affords an efficient separation of the components of said clarified solution, as will be exemplified below, the fraction containing exclusively 1,3-propanediol being eluted in the first chromatographic fractions.

In a second embodiment of the process according to the invention, the cation is selected from the group consisting of zinc and aluminum.

Here the inventors have found that the effect of this chromatographic separation is to remove all the 1,3-propanediol fermentation coproducts in the first fractions eluted, enabling said 1,3-propanediol to emerge in the last chromatographic fractions.

In this step of the process according to the invention, the inventors recommend combining any fractions containing glycerol as fermentation coproduct and treating them with microorganisms which are capable of converting the glycerol to 1,3-propanediol, so as to give a fraction enriched in 1,3-propanediol.

It is then possible to combine this 1,3-propanediol-enriched fraction with the above-mentioned fractions of purified 1,3-propanediol obtained in the chromatographic separation step.

It is preferable, however, to reinject said 1,3-propanediol-enriched fraction upstream of the chromatographic separation in order to complete its purification, if necessary.

The last step of the process according to the invention consists in combining all the chromatographic fractions containing 1,3-propanediol.

Other characteristics and advantages of the invention will become apparent from the Examples which follow, although they are given here only by way of illustration and without implying a limitation.

EXAMPLE 1

A fermentation medium containing 90.5 g/l of 1,3-propanediol and 28.7 g/l of glycerol, obtained by fermenting a recombinant *E. coli* which produces 1,3-propanediol from glucose under conditions such as those described in patent application WO 96/35796, is subjected to microfiltration on a TECHSEP membrane of porosity 0.1 μm so as to remove the cells therefrom.

The fermentation was stopped at the point where all the glucose introduced had been consumed by the microorganism.

The resulting clarified aqueous solution still contains some cellular debris and an ionic load of 70 meq/l.

It is passed through a column of charcoal to remove the proteins, this being followed by a demineralization step to remove any residual ions still present in the fermentation medium, said step involving passage over a strong cationic resin and then over a weakly basic resin of the acrylic type.

The clarified solution deproteinized and desalinated in this way has a solids content of 12% by weight.

This solution is then subjected to chromatographic separation on a PUROLITE PCR 732 cation exchange resin consisting of polystyrenesulfonic acid crosslinked with 7% of divinylbenzene, in which the cation is lanthanum.

As this resin is initially a resin in the H' form, the cation is replaced by percolation of the resin with a 200 g/l solution of lanthanum chloride until more than 98% of the capacity of the column is in the lanthanum form, this being determined by following the pH of the solution leaving the column.

350 ml of this resin are then placed in a column with a height of 2 m and a cross-section of 15 $mm^2$.

2.3 ml of the deproteinized and desalinated clarified solution are applied to said column, elution being carried out using water introduced at a rate of 3 ml/min.

The temperature of the system is fixed at 65° C.

The constituents of the fractions collected at the column outlet are detected using an R401 refractometric detector marketed by WATERS, connected to a plotter, and are analyzed by HPLC on a BCX6 column in the calcium form containing 6% of DVB, marketed by BIORAD, coupled to a refractometric detector.

This procedure gives a first fraction of 39 ml containing 2.0 g/l of 1,3-propanediol (i.e. a yield of 31.9%, this percentage being expressed relative to the amount by weight of compounds eluted from said column).

The other two fractions respectively comprise the following:

51 ml of a mixture containing 0.8 g/l of glycerol and 2.7 g/l of 1,3-propanediol (i.e. a yield of 57.9%), 50 ml containing 0.5 g/l of glycerol (i.e. a yield of 8.5%).

These two fractions were collected and then treated with *Clostridium butyricum* NRRL B-1024 bacteria immobilized in the form of LENTIKATS®, supplied by GENIALAB TECHNOLOGIE.

Total conversion of the glycerol was carried out, making it possible to combine all the fractions containing 1,3-propanediol into a solution of high purity.

EXAMPLE 2

The chromatographic separation was carried out under the same operating conditions as in Example 1, except that the cationic resin was lead.

This procedure gives a first fraction of 48 ml containing 3.0 g/l of 1,3-propanediol (i.e. a yield of 47%, this percentage being expressed relative to the amount by weight of compounds eluted from said column).

The other two fractions respectively comprise the following:

54 ml of a mixture containing 0.7 g/l of glycerol and 1.4 g/l of 1,3-propanediol (i.e. a yield of 37.5%), 70 ml containing 0.5 g/l of glycerol (i.e. a yield of 11%).

Total conversion of the glycerol was carried out with *Clostridium butyricum* NRRL B-1024 bacteria immobilized in the form of LENTIKATS®, making it possible to combine all the fractions containing 1,3-propanediol into a solution of high purity.

What is claimed is:

1. A process for the purification of 1,3-propanediol from a fermentation medium of a 1,3-propanediol-producing microorganism, the fermentation medium comprising the 1,3-propanediol-producing microorganism, 1,3-propanediol and fermentation coproducts consisting at least of glycerol, wherein:

a) the 1,3-propanediol-producing microorganism is separated from the other components of the fermentation medium to give a clarified aqueous solution;

b) said clarified aqueous solution is passed over a cation exchange resin to give at least one fraction comprising purified 1,3-propanediol and at least one fraction comprising the fermentation coproducts, the cation in the cation exchange resin being selected from the group consisting of lanthanum, lead, iron, zinc and aluminum; and c) the 1,3-propandiol is recovered.

2. The process according to claim 1, wherein the clarified aqueous solution of step a) is passed through a column of charcoal and demineralized on a strong cationic resin and then on a weakly and/or strongly basic anionic resin.

3. The process according to claim 1, wherein the clarified aqueous solution of step a) is treated with a microorganism which converts the glycerol to 1,3-propanediol.

4. The process according to claim 1, wherein the chromatographic fraction of step b) comprising the fermentation coproducts, are treated with a microorganism which converts the glycerol in the fermentation coproducts to 1,3-propanediol.

5. The process according to claim 4, wherein the said fractions are reintroduced upstream of the chromatographic separation step.

6. The process according to claim 4, wherein the microorganism which converts the glycerol to 1,3-propanediol is selected from the group consisting of microorganisms of the genera Klebsiella, Citrobacter, Clostridium, Lactobacillus, Ilyobacter, Pelobacter and Enterobacter.

7. The process according to claim 6, wherein the microorganism is a Citrobacter or a Clostridium.

8. The process according to claim 4, wherein the microorganism which converts the glycerol to 1,3-propanediol is present in the fermentation medium in a free or an immobilized form.

9. The process of claim 8, wherein the microorganism is present in the immobilized form.

* * * * *